(12) United States Patent
Nasu

(10) Patent No.: US 8,119,108 B2
(45) Date of Patent: Feb. 21, 2012

(54) DISPERSION OF MICROPARTICULATE TITANIUM OXIDE AND COSMETICS CONTAINING THE SAME

(75) Inventor: Akio Nasu, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 893 days.

(21) Appl. No.: 12/097,330

(22) PCT Filed: Nov. 20, 2006

(86) PCT No.: PCT/JP2006/323079
§ 371 (c)(1),
(2), (4) Date: Jun. 19, 2008

(87) PCT Pub. No.: WO2007/069430
PCT Pub. Date: Jun. 21, 2007

(65) Prior Publication Data
US 2009/0169496 A1    Jul. 2, 2009

(30) Foreign Application Priority Data

Dec. 14, 2005    (JP) ................. 2005-360471

(51) Int. Cl.
| | |
|---|---|
| A61Q 17/00 | (2006.01) |
| A61Q 17/04 | (2006.01) |
| A61K 8/00 | (2006.01) |
| A61K 8/02 | (2006.01) |
| A61K 8/04 | (2006.01) |
| A61K 8/18 | (2006.01) |
| A61K 33/00 | (2006.01) |

(52) U.S. Cl. ................. 424/59; 424/401; 424/600
(58) Field of Classification Search ............ 424/59, 424/401, 600
See application file for complete search history.

(56) References Cited

U.S. PATENT DOCUMENTS
| | | | |
|---|---|---|---|
| 4,927,464 A | 5/1990 | Cowie | |
| 5,599,529 A | 2/1997 | Cowie | |
| 6,197,282 B1 | 3/2001 | Oshima et al. | |
| 2009/0269377 A1* | 10/2009 | Lu | 424/401 |

FOREIGN PATENT DOCUMENTS
| | | |
|---|---|---|
| EP | 0801941 A1 | 10/1997 |
| EP | 1847262 A1 | 10/2007 |
| JP | 9-208438 | 8/1997 |
| JP | 09-208438 A | 8/1997 |
| JP | 11-116454 | 4/1999 |
| JP | 2002-80771 | 3/2002 |
| JP | 2002-080771 A | 3/2002 |
| JP | 2004-001862 A | 1/2004 |
| JP | 2004-2887 | 1/2004 |
| JP | 2004-035632 A | 2/2004 |
| JP | 2005-154736 | 6/2005 |
| JP | 2006-131547 | 5/2006 |
| JP | 2007-22972 | 2/2007 |
| WO | 97/45097 | 12/1997 |
| WO | 02/00797 A1 | 1/2002 |
| WO | 20061075679 A1 | 7/2006 |

OTHER PUBLICATIONS

Translation of JP H09-208438, nine pages.
Translation of JP 2002-80771, 15 pages.
Translation of JP 2004-2887, 18 pages.
Translation of JP H2004-235632, 11 pages.
International Search Report for PCT/JP2006/323079 mailed Feb. 20, 2007, three pages.
Japanese Patent Abstract Publication No. 11-116454 published Apr. 27, 1999, ten pages.
Japanese Patent Abstract Publication No. 2005-154736 published Jun. 16, 2005, 25 pages.
Japanese Patent Abstract Publication No. 2006-131547 published May 25, 2006, 14 pages.
Japanese Patent Abstract Publication No. 2007-022972 published Feb. 1, 2007, 22 pages.
European Search Report dated May 31, 2011; 06832940.8-2 974717 PCT/JP2006323079; Shiseido Company Limited (5 pages).
Patent Abstracts of Japan, Publication No. 09-208438, published Aug. 12, 1997, Applicant—Ishihara Sangyo Kaisha Ltd., (7 pages).
Patent Abstracts of Japan, Publication No. 2002-080771, publishe.d Mar. 19, 2002, Applicant—Noevir Co Ltd., (11 pages).
Patent Abstracts of Japan, Publication No. 2004-001862, published Jan. 8, 2004, Applicant—Nihon Yamamura Glass Co Ltd., (16 pages).
Patent Abstracts of Japan, Publication No. 2004-035632, published Feb. 5, 2004, Applicant—Tayca Corporation, (9 pages).

* cited by examiner

Primary Examiner — James H. Alstrum-Acevedo
(74) Attorney, Agent, or Firm — Rankin, Hill & Clark LLP

(57) ABSTRACT

The present invention provides a dispersion of microparticulate titanium oxide that can generate a natural finish feeling, which includes a feeling of transparency, and has good long-term stability and an excellent UV protective effect in both UVA and UVB regions. The present invention is a dispersion of microparticulate titanium oxide characterized in that the microparticulate titanium oxide with the average major axis of 30 to 100 nm and the average minor axis of 8 to 50 nm is dispersed, by maintaining the average size of dispersed particles to be 80 to 110 nm, in a hydrophobic dispersion medium. In the dispersion of microparticulate titanium oxide, the content of silicone oil relative to the total hydrophobic dispersion medium is preferably 10 to 100 weight %. Furthermore, it is preferable that the dispersion of microparticulate titanium oxide contains a biterminally-siliconized polyglycerin as a dispersant. The dispersion of microparticulate titanium oxide can be preferably contained in a cosmetic.

4 Claims, 2 Drawing Sheets

DISPERSION OF MICROPARTICULATE TITANIUM OXIDE AND COSMETICS CONTAINING THE SAME

RELATED APPLICATIONS

This application claims the priority of Japanese Patent Application No. 2005-360471 filed on Dec. 14, 2005, which is incorporated herein by reference.

TECHNICAL FIELD

The present invention relates to a dispersion of microparticulate titanium and cosmetics containing the same, and in particular, relates to a dispersion of microparticulate titanium dispersed in an oil dispersion medium.

BACKGROUND ART

Ultraviolet light is classified into long-wavelength UV light (UVA), the wavelength of which is 320 to 400 nm, middle-wavelength UV light (UVB), the wavelength of which is 290 to 320 nm, and short-wavelength UV light (UVC), the wavelength of which is below 290 nm.

Among them, UVA and UVB reach the Earth's surface without being absorbed or scattered by the ozone layer and cause various harmful effects. Specifically, it is known that UVB induces erythema, bulla, etc. In addition, it has been clarified that UVA not only induces a suntan on the skin but also lowers systemic immune function and triggers skin cancer.

In order to prevent the harmful effects to the human body, various UV protection agents have been developed. In particular, titanium oxide is most frequently used in the fields of cosmetics, paints, and chemical fibers as the UV protection agent that is chemically and physically stable and highly safe.

The shielding of UV light with titanium oxide is achieved by the absorption and scattering of UV light.

(1) Absorption Effect

Titanium oxide has electrically a semiconductor structure, and the valence band and the conduction band are not continuous. Therefore, titanium oxide absorbs light of a wavelength that corresponds to the energy higher than the band-gap, which is the energy difference between the two levels. Titanium oxide mainly absorbs UV in the UVB region.

(2) Scattering Effect

The light scattering ability of titanium oxide is dependent on the relationship between the particle size and the wavelength of light. If the particle size of microparticulate titanium oxide is comparable to the wavelength of light, Mie scattering takes place and the maximum is reached in the vicinity of ½ wavelength. If the particle size is smaller than that (less than about 1/10 wavelength), Rayleigh scattering takes place and its scattering ability is inversely proportional to the fourth power of the wavelength.

Therefore, it is necessary to suitably control the particle size in order to maintain transmission in the visible region and effectively shield UV light.

In recent years, sufficiently small microparticulate titanium oxide (less than 100 nm) compared with the wavelength of visible light is predominantly used so that the scattering of visible light is low from the standpoint of transparency.

In patent literatures 1 to 4, for example, dispersions in which microparticulate titanium oxide is dispersed in an oil dispersion medium are disclosed.

Patent literature 1: Japanese Unexamined Patent Publication No. H09-208438
Patent literature 2: Japanese Unexamined Patent Publication No. 2002-80771
Patent literature 3: Japanese Unexamined Patent Publication No. 2004-2887
Patent literature 4: Japanese Unexamined Patent Publication No. 2004-35632

DISCLOSURE OF THE INVENTION

Problem to be Solved by the Invention

In the particle size range where the scattering of visible light is small, however, not only the scattering of visible light but also the scattering of UV light (in particular UVA) is often small, and it was difficult to achieve both high transparency and excellent shielding of UV light.

In addition, the aggregation force between particles of microparticulate titanium oxide is strong. Thus, no matter how small the primary particles are, they often aggregate in the composition and form large secondary particles. Therefore, when they were used in cosmetics, the color sometimes became dull, a feeling of transparency was sometimes lost, and the spreadability during application sometimes became poor. Even when the amount of blending was increased, the expected UV protective effect occasionally could not be obtained.

An object of the present invention is to provide a dispersion of microparticulate titanium oxide that can generate a natural finish feeling, which includes a feeling of transparency, and has good long-term stability and an excellent UV protective effect in both UVA and UVB regions.

Means to Solve the Problem

In view of the above problems, the present inventors have studied diligently. As a result, the present inventors found that a dispersion of microparticulate titanium oxide with excellent UV protective ability in both UVA and UVB regions, while maintaining a feeling of transparency, and good long-term stability without reaggregation could be obtained by specifying both primary particle size and the size of dispersed particles, thus leading to completion of the present invention.

That is, the first subject of the present invention is a dispersion of microparticulate titanium oxide characterized in that the microparticulate titanium oxide with the average major axis of 30 to 100 nm and the average minor axis of 8 to 50 nm is dispersed, by maintaining the average size of dispersed particles to be 80 to 110 nm, in a hydrophobic dispersion medium.

In the dispersion of microparticulate titanium oxide, the content of silicone oil relative to the total hydrophobic dispersion medium is preferably 10 to 100 weight %.

In addition, it is preferable that the dispersion of microparticulate titanium oxide contains a biterminally-siliconized polyglycerin as a dispersant.

The second subject of the present invention is cosmetics containing the dispersion of microparticulate titanium oxide.

Effect of the Invention

In the present invention, a dispersion of microparticulate titanium oxide with an excellent feeling of transparency, excellent UV light protection, and good long-term stability can be obtained by maintaining the major axis to be 30 to 100 nm and the minor axis to be 8 to 50 nm, as the average primary particle size of microparticulate titanium oxide, and by maintaining the average size of dispersed particles to be 80 to 110 nm.

BEST MODE FOR CARRYING OUT THE INVENTION

Figure 1:
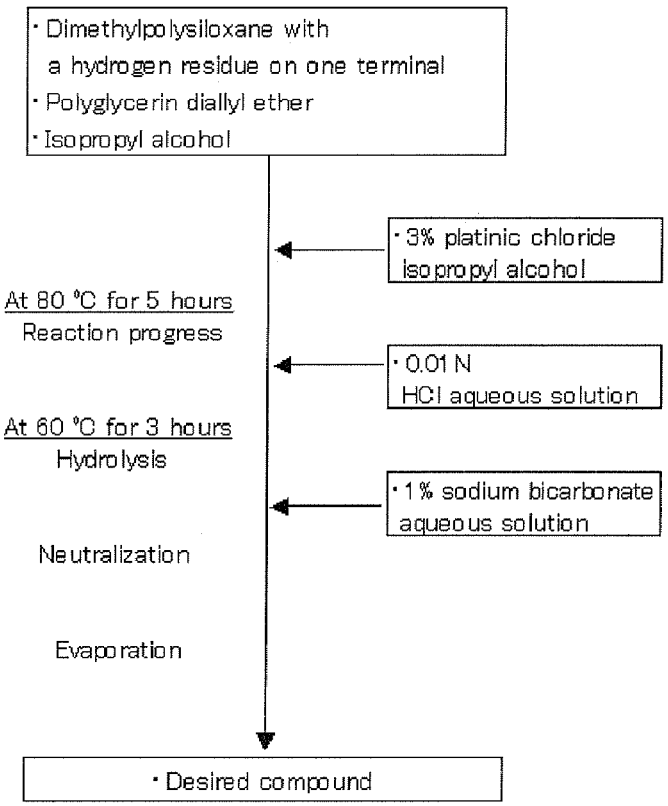
FIG. 1 shows a synthesis scheme for the biterminally-siliconized polyglycerin that is obtained through ether bonding.

In the following, an embodiment of the present invention is described in detail.
1. Dispersion of Microparticulate Titanium Oxide The dispersion of microparticulate titanium oxide of the present invention is a dispersion in which microparticulate titanium oxide with the average major axis of 30 to 100 nm and the average minor axis of 8 to 50 nm is dispersed, by maintaining the average size of dispersed particles to be 80 to 110 nm, in a hydrophobic dispersion medium.
[Microparticulate Titanium Oxide]

The microparticulate titanium oxide of the present invention is characterized in that the average minor axis is 8 to 50 nm and the average major axis is 30 to 100 nm. In the cases of either larger or smaller sizes than these sizes, the UV shielding effect is low, and it is necessary to increase the amount of blending. If the particle size is too small, the aggregation force between particles is strong and it is difficult to achieve good dispersion.

The shape and crystalline state of microparticulate titanium oxide can be arbitrary, and the selection can be made depending on the purpose. For example, a shape such as a granular (spherical), needle-like, spindle-shaped, plate-like, or flaky shape; and an amorphous state or a crystalline state such as anatase or rutile can be suitably selected for use.

In particular, it is preferable that the average minor axis of microparticulate titanium oxide is 30 to 50 nm. In addition, the ratio of the average major axis and the average minor axis is preferably from 1 to 5, and more preferably from 2.5 to 5.

Microparticulate titanium oxide can be also used by hydrophobizing the surface, as necessary, by a publicly known method.

The hydrophobizing agent is not limited in particular, and any publicly known hydrophobizing agent can be used. Specific examples include silicone compounds such as dimethylpolysiloxane, methylhydrogenpolysiloxane, and methylphenylpolysiloxane; fluorine compounds such as perfluoroalkyl group-containing esters, perfluoropolyethers, and perfluoroalkyl group-containing polymers; oils and fats such as liquid paraffin, squalane, petrolatum, lanolin, microcrystalline wax, and polyethylene wax; metallic soaps such as aluminum laurate and aluminum stearate; organic titanate compounds such as isopropyltriisostearoyl titanate; and silane coupling agents such as perfluoroalkyl silane and octyltriethoxysilane. One or more of these agents can be used.
[Hydrophobic Dispersion Media]

Examples of hydrophobic dispersion media used in the present invention include hydrocarbon oils such as liquid paraffins, squalane, isoparaffins, branched chain light paraffins, petrolatum, and ceresin; ester oils such as isopropyl myristate, cetyl isooctanoate, and glyceryl trioctanoate; and silicone oils such as decamethylpentasiloxane, dimethylpolysiloxane, and methylphenylpolysiloxane.

In the present invention, a silicone oil is preferably used as a hydrophobic dispersion medium. Specifically, the content of silicone oil with respect to the total hydrophobic dispersion medium is preferably 10 to 100 weight %, more preferably 50 to 100 weight %, and further more preferably 70 to 100 weight %.

The silicone oil used is not limited in particular so far as the effect of the present invention is not undermined, and linear polysiloxanes, cyclic polysiloxanes, modified silicones, silicone resins, etc. can be used. In particular, silicone oils with a boiling point of 200° C. or less at normal pressure are preferable. Examples of silicone oils include linear polysiloxanes such as dimethylpolysiloxane, methylphenylpolysiloxane, and methylhydrogenpolysiloxane; and cyclic polysiloxanes such as octamethylcyclotetrasiloxane, decamethylcyclopentasiloxane, dodecamethylcyclohexasiloxane, and tetramethyltetrahydrogencyclotetrasiloxane.

Among them, volatile silicone oils such as volatile linear polysiloxanes like dimethylpolysiloxane with a low degree of polymerization (degree of polymerization: 3 to 7); or volatile cyclic polysiloxanes like decamethylcyclopentasiloxane and octamethylcyclotetrasiloxane are especially desirable because an oily sensation hardly remains upon their application on the skin and a fresh feeling in use can be achieved.
[Dispersants]

In the present invention, a dispersant can be used to improve the dispersibility of microparticulate titanium oxide and to improve the long-term stability of dispersion. The dispersant is not limited in particular so far as it is soluble in a hydrophobic dispersion medium. Examples of dispersants include polyoxyethylene alkyl ethers, sorbitan fatty acid esters, polyoxyethylene alkylphosphate esters, fatty acid alkanolamides, polyether-modified silicone oils, and silicone resins. These dispersants may be used either alone or in combination of two or more.

As a dispersant, a biterminally-siliconized polyglycerin is preferably used. When a biterminally-siliconized polyglycerin is used as a dispersant, the long-term stability of the dispersion can be improved.

Examples of biterminally-siliconized polyglycerins include those represented by the below-described general formula (a).
General formula (a):

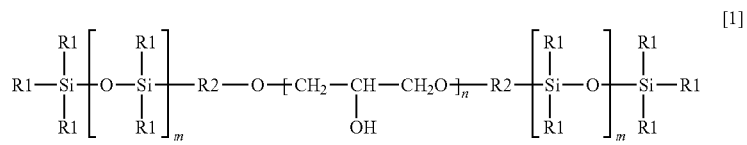

In the formula, R1 is a linear or branched alkyl group of 1 to 12 carbon atoms or a phenyl group, R2 is an alkylene group of 2 to 11 carbon atoms, m is 10 to 120, and n is 1 to 11.

Examples of preferable biterminally-siliconized polyglycerins include biterminally-siliconized polyglycerins represented by the below-described general formula (b).

General Formula (b):

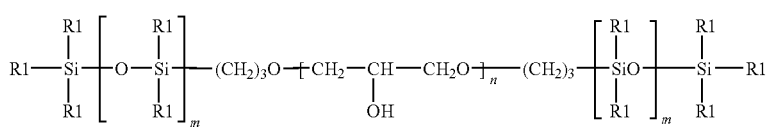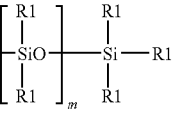

In the formula, R1 is a linear or branched alkyl group of 1 to 12 carbon atoms or a phenyl group, m is 10 to 120, and n is 1 to 11.

The basic structure of the biterminally-siliconized polyglycerin is that of a BAB-type triblock copolymer. For example, a silicone with a hydrogen residue on one terminal, represented by the below-described structural formula (c), may be used as B.

A is a polyglycerin residue.

The silicone with a hydrogen residue on one terminal represented by the below-described structural formula (c) is a publicly known compound. A BAB-type triblock copolymer with any degree of polymerization can be prepared by a publicly known method.

Structural Formula (c):

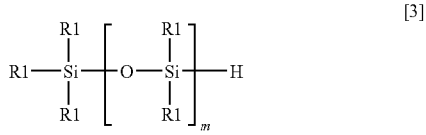

In the formula, each R1 is a linear or branched alkyl group of 1 to 12 carbon atoms or a phenyl group, and m is 10 to 120.

Although the bonding between A and B is not an essential part of the structure for the present invention, the biterminally-siliconized polyglycerin that is exemplified in the present invention is prepared by bonding, through an ether linkage, a compound of the above-described structural formula (c) and a compound of the below-described structural formula (d) with the use of a platinum catalyst.

Structural Formula (d):

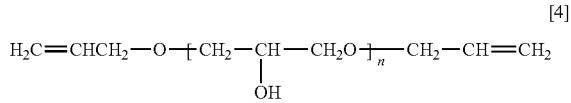

In the formula, n is 1 to 1.

The BAB-type triblock copolymer can be synthesized by a publicly known method. The synthesis scheme is shown in FIG. 1.

Thus, biterminally-siliconized polyglycerins represented by the above-described general formulas (a) and (b) can be obtained.

The degree of polymerization of the silicone chain (m) is preferably 10 to 120, and the side-chain substituent may be a methyl group, a phenyl group, or an alkyl group.

The degree of polymerization of the polyglycerin chain (n) is preferably 1 to 11.

It is considered that a significant stability effect of a dispersion can be achieved because the biterminally-siliconized polyglycerin has dispersion sites of silicone chains at both ends; the polymer expands in a dispersion medium solvent by retaining microparticulate titanium oxide at the adsorption sites of the highly adsorptive polyglycerin chain.

Figure 2:
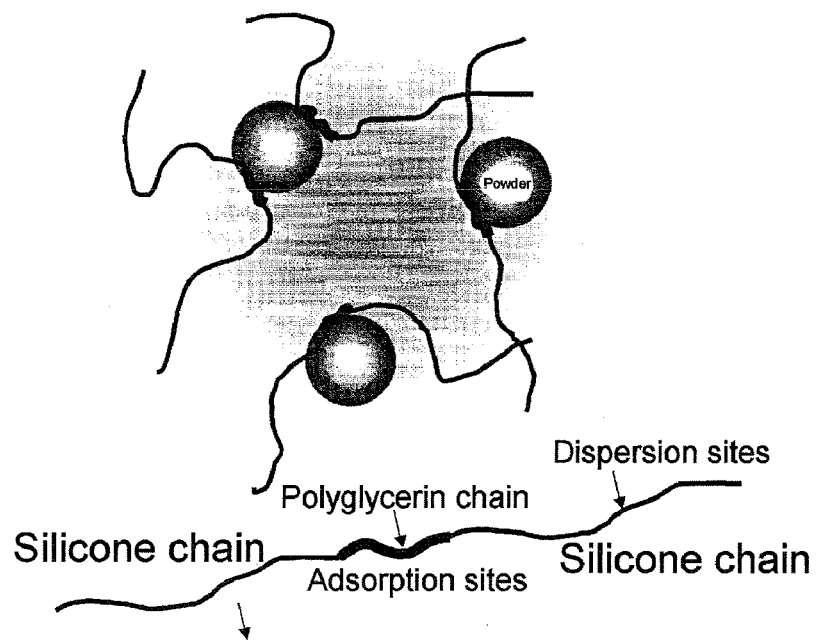
FIG. 2 shows a schematic figure that illustrates the stability of microparticulate titanium oxide dispersion when a biterminally-siliconized polyglycerin was used as a dispersant.

As shown in FIG. 2, for the manifestation of functionality of the biterminally-siliconized polyglycerin, the solubility of the B-block into the solvent and the high adsorptivity of the A-block chain to the powder surface are important. That is, it is essential that the hydrophilic-lipophilic balance (HLB) of A and B blocks is within a suitable range for the manifestation of functionality. The HLB value can be determined by a publicly known method, for example, it is calculated with the Griffin equation (HLB value=molecular weight of polyglycerin part 20/total molecular weight). In the present invention, it is preferable that the HLB of the biterminally-siliconized polyglycerin is 0.2 to 3.0.

The expansion of B-block chains, which prevent the aggregation of powder particles, is dependent on the molecular weight of the polymer. The higher the molecular weight of the B-block chain, the higher the prevention effect of aggregation. On the other hand, the adsorption to powder is considered due to weak forces such as van der Waals force of the A-block chain. Nevertheless, a satisfactory adsorption force can be obtained at a relatively low molecular weight because a strong adsorption force can be obtained by using polyglycerins, for the A-block chain, compared with polyethylene glycols. When the molecular weights of both A and B blocks are too high, it may be difficult to spread a powder dispersion composition, and the feeling in spreading may be heavy during application. Thus, there is an appropriate range for the molecular weight, and the molecular weight of the biterminally-siliconized polyglycerin in the present invention is preferably 2000 to 20000.

The amount of blended dispersant is preferably 1 to 40 weight % with respect to the amount of microparticulate titanium oxide, and more preferably 5 to 30 weight %. When the amount of blended dispersant is less than 1 weight %, the addition effect is not satisfactory. When the amount of the blended dispersant exceeds 40 weight %, no significant increase in the effect is observed.

The dispersion of the present invention can be obtained by adding microparticulate titanium oxide and a dispersant, as necessary, to a hydrophobic dispersion medium and by performing dispersion with a disperser. For dispersion, a disperser with powerful dispersing ability such as a paint shaker, sand mill, roller mill, bead mill, or high-pressure homogenizer is suitably selected for use. A dispersion of the present invention cannot be achieved with a Disper or homomixer.

Before dispersion, preliminary mixing may be conducted with a Disper or homomixer.

During dispersion, the amount of microparticulate titanium oxide is preferably 10 to 70 weight % of the total amount, and more preferably 20 to 50 weight %. If the amount is less than 10 weight % or exceeds 70 weight %, it may be difficult to achieve dispersion.

In the dispersion of microparticulate titanium oxide of the present invention, microparticulate titanium oxide with the average major axis of 30 to 100 nm and the average minor axis of 8 to 50 nm is dispersed, by maintaining the average size of dispersed particles to be 80 to 110 nm, in a hydrophobic dispersion medium. Therefore, the transmittance of visible light is high, and the transmittance of UVA and UVB is low. Specifically, in 10 weight % dispersion of microparticulate titanium oxide, the transmittance is 90% or higher at a wavelength of 550 nm, the transmittance is less than 25% at a wavelength of 360 nm, and the transmittance is less than 0.5% at a wavelength of 300 nm.

When the average size of dispersed particles exceeds 110 nm, the shielding of UV light (in particular UVA) and the transparency are poor. On the other hand, in order to allow the average size of dispersed particles to be less than 80 nm, the time necessary for dispersion is too long and it is not realistic. In addition, the reaggregation of titanium oxide particles takes place in cosmetics.

When a biterminally-siliconized polyglycerin is used as a dispersant, the suppression effect of the aggregation, which normally takes place over time, of microparticulate titanium oxide becomes higher. As a result, good UV protective ability and the transparency can be retained after long-term storage.

2. Cosmetics

When the dispersion of microparticulate titanium oxide of the present invention is applied to various products such as cosmetics, it can be used as it is or it is diluted with an oil component to prepare an oil product. These can be further emulsified with an aqueous component, by a publicly known method, to obtain an emulsion product.

The concentration of microparticulate titanium oxide in cosmetics is not limited in particular, and it can suitably be adjusted as necessary.

In order to achieve an excellent UV protective effect in both UVA and UVB regions, it is preferable to blend a dispersion of microparticulate titanium oxide so that the content of microparticulate titanium oxide in a cosmetic is 1 weight % or higher, and more preferably 3 weight % or higher.

The cosmetics of the present invention contain a dispersion of microparticulate titanium oxide, whose primary particle size and the size of dispersed particles have been adjusted. Therefore, even when the content of titanium oxide is small, an excellent UV protective effect can be achieved. On the other hand, when the content of microparticulate titanium oxide in cosmetics is 10 weight % or higher or even when the content is 20 weight % or higher, a feeling of transparency will not be lost.

In the cosmetics of the present invention, other cosmetic components can be blended so far as the effect of the present invention is not undermined. Specific examples include powders such as inorganic powder (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate, calcium phosphate, fluorine apatite, hydroxyapatite, ceramic powder, metallic soap (for example, zinc myristate, calcium palimitate, and aluminum stearate), and boron nitride, etc); organic powder (for example, polyamide resin powder (nylon powder), polyethylene powder, polymethylmethacrylate powder, polystyrene powder, styrene-acrylic acid copolymer powder, benzoguanamine resin powder, poly(tetrafluoroethylene) powder, and cellulose powder, etc); inorganic white family pigment (for example, zinc oxide, etc); inorganic red family pigment (for example, iron oxide (colcothar), and iron titanate, etc); inorganic brown family pigment (for example, γ-iron oxide, etc); inorganic yellow family pigment (for example, yellow iron oxide, and loess, etc); inorganic black family pigment (for example, black iron oxide, and lower titanium oxide, etc); inorganic purple family pigment (for example, mango violet, cobalt violet, etc); inorganic green family pigment (for example, chrome oxide, chrome hydroxide, cobalt titanate, etc); inorganic blue family pigment (for example, ultramarine, iron blue, etc); pearl pigment (for example, titanium oxide coated mica, titanium oxide coated bismuth oxychloride, titanium oxide coated talc, colored titanium oxide coated mica, bismuth oxychloride, argentine, etc); metal powder pigment (aluminum powder, copper powder, etc); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Red No. 201, Orange No. 203, Orange No. 204, Yellow No. 205, Yellow No. 401, Blue No. 401, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, etc); natural pigment (for example, chlorophyll, β-carotene, etc), etc.

In the cosmetics of the present invention, one kind or more than one kind of organic ultraviolet light absorbers can be blended.

Examples of ultraviolet light absorbers include benzotriazol family ultraviolet light absorbers (2,2'-hydroxy-5-methylphenylbenzotriazol, 2-(2'-hydroxy-5'-t-octylphenyl) benzotriazol, and 2-(2'-hydroxy-5'-methylphenylbenzotriazol); benzoylmethane family ultraviolet light absorbers (dibenzalazine, dianisoylmethane, 4-t-butyl-4'-methoxydibenzoylmethane, 1-(4'-isopropylphenyl)-3-phenylpropane-1,3-dion, and 5-(3,3-dimethyl-2-norbornylidene)-3-pentane-2-one); benzoic acid family ultraviolet light absorbers (p-aminobenzoic acid (PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc.); anthranilic acid family ultraviolet light absorbers (homomethyl N-acetylanthranilate etc.); salicylic acid family ultraviolet light absorbers (amyl salicylate, menthyl salicylate, homomethyl salicylate, octyl salicylate, phenyl salicylate, benzyl salicylate, p-isopropanolphenyl salicylate, etc.) cinnamic acid family ultraviolet light absorbers (for example, octyl methoxycinnamate, di-p-methoxycinnamic acid-mono-2-ethylhexanoic acid glyceryl, octylcinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc.); silicone family cinnamic acid ultraviolet light absorbers ([3-bis(trimethylsiloxy)methylsilyl-1-methylpropyl]-3,4,5-trimethoxycinnamate, [3-bis(trimethylsiloxy)methylsilyl-3-methylpropyl]-3,4,5-trimethoxycinnamate, [3-bis(trimethylsiloxy)methylsilylpropyl]-3,4,5-trimethoxycinnamate, [3-bis(trimethylsiloxy)methylsilylbutyl]-3,4,5-trimethoxycinnamate, [3-tris(trimethylsiloxy)silylbutyl]-3,4,5-trimethoxycinnamate, [3-tris(trimethylsiloxy)silyl-1- methylpropyl]-3,4-dimethoxycinnamate); 3-(4-methylbenzylidene)-d,l-camphor 3-benzylidene-d,l-camphor; urocanic acid, urocanic acid ethyl ester, 2-phenyl-5-methylbenzoxazol, 5-(3,3'-dimethyl-2-norbornylidene)₃-pentane-2-one, silicone modified ultraviolet light absorbers; fluorine modified ultraviolet light absorbers.

Other components normally can be blended. Examples include liquid fat, solid fat, wax, higher fatty acids, higher alcohols, anionic surfactants, cationic surfactants, amphoteric surfactants, nonionic surfactants, moisturizer, water-soluble polymers, thickener, film-forming agents, metal ion sequestering agents, lower alcohols, polyhydric alcohols, saccharides, amino acids, organic amines, polymer emulsion, pH adjuster, skin nutrients, vitamins, antioxidants, antioxidant promoters, perfume, and water. The cosmetics can be prepared by ordinary methods according to the desired form.

The cosmetics of the present invention can be provided in any form such as a solution form, solubilized form, emulsion form, water-oil double layer, gel, aerosol, mist, or capsule.

The cosmetic products of the present invention can also be in any form so far as they are conventional skin external preparations: facial cosmetics such as lotion, milky lotion, cream, and packs; makeup cosmetics such as pre-makeup, foundation, cheek color, lipstick, lip cream, eye shadow, eye liner, mascara, and sunscreen; body cosmetics; aromatic cosmetics; skin cleansers such as makeup remover, facial cleanser, and body shampoo; and hair care cosmetics such as hair spray, hair cream, hair lotion, hair rinse, and shampoo.

In particular, it is preferably used as a product to prevent UV light.

In addition, the dispersion of microparticulate titanium oxide of the present invention is applicable, in addition to cosmetics, to other uses such as resin compositions, paint, ink, coating compositions, etc.

The present invention will hereafter be described in detail with reference to examples. However, the present invention is not limited by these examples. Unless otherwise noted, the blending quantity is expressed in weight % with respect to the system into which the component is blended.

EXAMPLES

Embodiment 1

Initially, the evaluation criteria for the present examples will be explained.

Each dispersion is applied on a quartz plate with an applicator so that the film thickness will be 10 μm, and the transmittance is measured with a spectrophotometer. In addition, a visual observation is conducted.

(1) UVB Protective Ability
○: The light transmittance at a wavelength of 300 nm is less than 0.5%.
Δ: The light transmittance at a wavelength of 300 nm is 0.5% or higher and less than 2.0%.
X: The light transmittance at a wavelength of 300 nm is 2.0% or higher.

(2) UVA Protective Ability
○: The light transmittance at a wavelength of 360 nm is less than 25%.
Δ: The light transmittance at a wavelength of 360 nm is 25% or higher and less than 30%.
X: The light transmittance at a wavelength of 360 nm is 30% or higher.

(3) Transparency (Visible Light Transmission)
○: The light transmittance at a wavelength of 550 nm is 90% or higher.
Δ: The light transmittance at a wavelength of 550 nm is 80% or higher and less than 90%.
X: The light transmittance at a wavelength of 550 nm is less than 80%.

(4) Visual Observation
○: transparent
Δ: slightly whitish
X: whitish (5) Long-Term Stability
Each dispersion is stored in a constant-temperature bath at 25° C. for 3 months, and the state of dispersion is observed after storage.
○: no aggregation or sedimentation of powder
Δ: some aggregation and sedimentation of powder
X: aggregation and sedimentation of powder The titanium oxide dispersions of the below-described test examples were evaluated based on the above-described criteria.

Test Examples 1-1 to 1-3

By mixing and stirring 1.0 g of microparticulate titanium oxide with various average particle sizes and 9.0 g of decamethylcyclopentasiloxane, respectively, with a homomixer, 10 weight % titanium oxide dispersions were obtained.

Test Examples 1-4 to 1-6

Commercial 10 weight % titanium oxide dispersions (solvent: decamethylcyclopentasiloxane) with various average particle sizes were used.

The results are shown in Table 1.

TABLE 1

| | Test example | | | | | |
|---|---|---|---|---|---|---|
| | 1-1 | 1-2 | 1-3 | 1-4 | 1-5 | 1-6 |
| Average particle sizes of titanium oxide (nm) | 50 | 35 | 15 | 50 | 35 | 15 |
| (1) UVB protective ability | ○ | ○ | ○ | ○ | ○ | ○ |
| (2) UVA protective ability | ○ | ○ | ○ | Δ | Δ | Δ |
| (3) Transparency (visible light transmission) | X | Δ | Δ | Δ | ○ | ○ |
| (4) Visual observation | Δ | Δ | Δ | Δ | ○ | ○ |
| (5) Long-term stability | X | X | X | ○ | ○ | ○ |

Even when the average particle sizes of titanium oxide were the same, there was a difference in the UV protective ability and the transparency among dispersions.

Thus, it was found that the UV protective ability and the transparency of dispersion were not uniformly determined by the primary particle size of titanium oxide alone.

Thus, the present inventors considered that the UV protective ability and the transparency are also related to the state of dispersion of microparticulate titanium oxide and conducted the following tests.

As described below, 40 weight % titanium oxide dispersions were prepared by changing the dispersion time and using microparticulate titanium oxide A (average major axis and average minor axis: 30 nm 8 nm).

To 5.5 g of decamethylcyclopentasiloxane, 4.0 g of microparticulate titanium oxide A and 0.5 g of biterminally-siliconized polyglycerin (Preparation Example 1) were added, and the dispersion was conducted with a paint shaker (zirconia beads with a diameter of 0.3 mm, filling rate: 50 vol %) for respective time lengths. This dispersion was diluted with decamethylcyclopentasiloxane so that the concentration of titanium oxide would be 20 weight %.

The sizes of dispersed particles were measured, for each dispersion, with the measurement apparatus for particle size distribution, Zetasizer-Nano of Malvern Instruments Ltd. In addition, the above-described evaluations (1) to (5) were also conducted.

The results are shown in Table 2.

TABLE 2

| | Test example | | | | | |
|---|---|---|---|---|---|---|
| | 2-1 | 2-2 | 2-3 | 2-4 | 2-5 | 2-6 |
| Dispersion time (h) | 0 | 1 | 3 | 5 | 8 | 15 |
| Average particle sizes of titanium oxide (nm) | 381.6 | 127.1 | 109.4 | 106.6 | 88.7 | 82 |
| (1) UVB protective ability | X | ○ | ○ | ○ | ○ | ○ |
| (2) UVA protective ability | Δ | Δ | ○ | ○ | ○ | ○ |
| (3) Transparency (visible light transmission) | X | Δ | ○ | ○ | ○ | ○ |
| (4) Visual observation | Δ | Δ | ○ | ○ | ○ | ○ |
| (5) Long-term stability | X | Δ | ○ | ○ | ○ | ○ |

Titanium oxide was aggregated and precipitated under a dispersion time of 0 hour, and there was no dispersion. Therefore, no UV protective ability was acquired not only in the UVA region but also in the UVB region.

When the dispersion time was allowed to be longer, the UV protective ability and the transparency improved. It was confirmed that a microparticulate titanium oxide dispersion excellent in the UV protective ability in both UVA and UVB regions, while maintaining a feeling of transparency, could be obtained when the average size of dispersed particles was 80 to 110 nm.

In order to allow the average size of dispersed particles to be less than 80 nm, the time necessary for dispersion is too long and it is not realistic. In addition, the reaggregation of titanium oxide particles may take place over time.

With the use of various types of microparticulate titanium oxide B to H, 10 weight % titanium oxide dispersions and 20 weight % titanium oxide dispersions were prepared in the same way as above by changing the dispersion time.

To 5.5 g of decamethylcyclopentasiloxane, 4.0 g of microparticulate titanium oxide and 0.5 g of biterminally-siliconized polyglycerin (Preparation Example 1) were added, and the dispersion was conducted with a paint shaker (zirconia beads with a diameter of 0.3 mm, filling rate: 50 vol %) for respective time lengths. This dispersion was diluted with decamethylcyclopentasiloxane.

TABLE 3

| | Test example | | | | | | |
|---|---|---|---|---|---|---|---|
| | 3 | 4 | 5 | 6 | 7 | 8 | 9 |
| Microparticulate titanium oxide | B | C | D | E | F | G | H |
| average major axis (nm) | 40 | 100 | 35 | 40 | 30 | 25 | 100 |
| average minor axis (nm) | 10 | 40 | 35 | 40 | 5 | 5 | 100 |
| | 20% | 10% | 10% | 10% | 20% | 20% | 10% |

These dispersions were also evaluated. The results are shown in Tables 4 to 10.

TABLE 4

| | Test example | | | | |
|---|---|---|---|---|---|
| | 3-1 | 3-2 | 3-3 | 3-4 | 3-5 |
| 20 weight % titanium oxide B dispersions (average major axis and average minor axis: 40 nm 10 nm) | | | | | |
| Dispersion time (h) | 0 | 1 | 3 | 5 | 8 |
| Average particle sizes of titanium oxide (nm) | 251.0 | 139.2 | 112.5 | 104.1 | 101.0 |
| (1) UVB protective ability | X | ○ | ○ | ○ | ○ |
| (2) UVA protective ability | Δ | Δ | Δ | ○ | ○ |
| (3) Transparency (visible light transmission) | X | Δ | Δ | ○ | ○ |
| (4) Visual observation | X | Δ | Δ | ○ | ○ |
| (5) Long-term stability | X | Δ | ○ | ○ | ○ |

TABLE 5

| | Test example | | | | |
|---|---|---|---|---|---|
| | 4-1 | 4-2 | 4-3 | 4-4 | 4-5 |
| 10 weight % titanium oxide C dispersions (average major axis and average minor axis: 100 nm 40 nm) | | | | | |
| Dispersion time (h) | 0 | 1 | 3 | 5 | 8 |
| Average particle sizes of titanium oxide (nm) | 947.0 | 139.2 | 125.1 | 110.3 | 105.1 |
| (1) UVB protective ability | X | Δ | ○ | ○ | ○ |
| (2) UVA protective ability | X | Δ | Δ | ○ | ○ |
| (3) Transparency (visible light transmission) | Δ | X | X | ○ | ○ |
| (4) Visual observation | Δ | X | X | ○ | ○ |
| (5) Long-term stability | X | Δ | Δ | ○ | ○ |

TABLE 6

| | Test example | | | | |
|---|---|---|---|---|---|
| | 5-1 | 5-2 | 5-3 | 5-4 | 5-5 |
| 10 weight % titanium oxide D dispersions (average major axis and average minor axis: 35 nm 35 nm) | | | | | |
| Dispersion time (h) | 0 | 1 | 3 | 5 | 8 |
| Average particle sizes of titanium oxide (nm) | 485.6 | 161.7 | 145.4 | 123.4 | 110.0 |
| (1) UVB protective ability | X | ○ | ○ | ○ | ○ |
| (2) UVA protective ability | Δ | Δ | Δ | ○ | ○ |
| (3) Transparency (visible light transmission) | X | Δ | Δ | Δ | ○ |
| (4) Visual observation | X | Δ | Δ | Δ | ○ |
| (5) Long-term stability | X | Δ | Δ | Δ | ○ |

TABLE 7

| | Test example | | | | |
|---|---|---|---|---|---|
| | 6-1 | 6-2 | 6-3 | 6-4 | 6-5 |
| 10 weight % titanium oxide E dispersions (average major axis and average minor axis: 40 nm 40 nm) | | | | | |
| Dispersion time (h) | 0 | 1 | 3 | 5 | 8 |
| Average particle sizes of titanium oxide (nm) | 376.6 | 163.7 | 154.8 | 149.1 | 109.1 |
| (1) UVB protective ability | X | Δ | ○ | ○ | ○ |
| (2) UVA protective ability | X | Δ | ○ | ○ | ○ |
| (3) Transparency (visible light transmission) | Δ | X | X | Δ | ○ |
| (4) Visual observation | Δ | X | X | Δ | ○ |
| (5) Long-term stability | X | Δ | Δ | Δ | ○ |

TABLE 8

| | Test example | | | | |
|---|---|---|---|---|---|
| | 7-1 | 7-2 | 7-3 | 7-4 | 7-5 |
| 20 weight % titanium oxide F dispersions (average major axis and average minor axis: 30 nm 5 nm) | | | | | |
| Dispersion time (h) | 0 | 1 | 3 | 5 | 8 |
| Average particle sizes of titanium oxide (nm) | 528.4 | 152.3 | 118.9 | 107.1 | 118.6 |
| (1) UVB protective ability | X | ◯ | ◯ | ◯ | ◯ |
| (2) UVA protective ability | X | ◯ | Δ | Δ | Δ |
| (3) Transparency (visible light transmission) | Δ | X | ◯ | ◯ | ◯ |
| (4) Visual observation | Δ | X | ◯ | ◯ | ◯ |
| (5) Long-term stability | X | Δ | Δ | Δ | X |

TABLE 9

| | Test example | | | | |
|---|---|---|---|---|---|
| | 8-1 | 8-2 | 8-3 | 8-4 | 8-5 |
| 20 weight % titanium oxide G dispersions (average major axis and average minor axis: 25 nm 5 nm) | | | | | |
| Dispersion time (h) | 0 | 1 | 3 | 5 | 8 |
| Average particle sizes of titanium oxide (nm) | 290.4 | 126.8 | 108.3 | 101.6 | 107.1 |
| (1) UVB protective ability | X | ◯ | ◯ | ◯ | ◯ |
| (2) UVA protective ability | X | ◯ | Δ | Δ | Δ |
| (3) Transparency (visible light transmission) | ◯ | Δ | Δ | ◯ | ◯ |
| (4) Visual observation | ◯ | Δ | Δ | ◯ | ◯ |
| (5) Long-term stability | X | Δ | Δ | Δ | X |

TABLE 10

| | Test example | | | | |
|---|---|---|---|---|---|
| | 9-1 | 9-2 | 9-3 | 9-4 | 9-5 |
| 10 weight % titanium oxide H dispersions (average major axis and average minor axis: 25 nm 5 nm) | | | | | |
| Dispersion time (h) | 0 | 1 | 3 | 5 | 8 |
| Average particle sizes of titanium oxide (nm) | 971 | 222 | 190 | 183 | 175 |
| (1) UVB protective ability | X | X | X | Δ | Δ |
| (2) UVA protective ability | Δ | Δ | ◯ | ◯ | ◯ |
| (3) Transparency (visible light transmission) | X | X | X | X | X |
| (4) Visual observation | X | X | X | X | Δ |
| (5) Long-term stability | X | X | Δ | Δ | ◯ |

Even when the average size of dispersed particles was 80 to 110 nm, the UVA shielding was not satisfactory if titanium oxide of types F to G was used. On the other hand, when titanium oxide of types B to E was used, both a feeling of transparency and the UVA and UVB protective effect were satisfactory.

With the use of titanium oxide of types F to G, the reaggregation of titanium oxide took place when the dispersion time was increased to 8 hours or higher. In the case of titanium oxide H, it was difficult to lower the size of dispersed particles to less than 110 nm even by increasing the dispersion time.

In light of this point, we have further investigated, and it was confirmed that both a feeling of transparency and the UVA and UVB protective effect became satisfactory when the average major axis of the primary particle size of microparticulate titanium oxide was 30 to 100 nm, the average minor axis was 10 to 50 nm, and the average size of dispersed particles was 80 to 110 nm.

When the primary particle size of microparticulate titanium oxide is smaller than the above-described range, the UVA shielding is not satisfactory even when the size of dispersed particles is 80 to 110 nm. On the other hand, when the primary particle size of microparticulate titanium oxide is larger than the above-described range, it is realistically difficult to let the size of dispersed particles to 80 to 110 nm by dispersing to the primary particles, and the UV shielding and the transparency are also not satisfactory.

When titanium oxide of types C to E was used, the same or higher UVA and UVB protective effect could be achieved though the content of titanium oxide was a half of that of titanium oxide of types F to G.

The general technology when we want to achieve both a feeling of transparency and the UV protective effect is to make the primary particle size as small as possible, highly disperse the particles, and blend a large amount of titanium oxide into cosmetics. In the present invention, we have succeeded to achieve both a feeling of transparency and the UV protective effect, even when the blended amount is small, by suitably dispersing the microparticulate titanium oxide having the primary particle size of a fixed range.

Embodiment 2

In the following, the relationship between the types of dispersants and the dispersibility was investigated.

To 5.5 g of decamethylcyclopentasiloxane, 4.0 g of microparticulate titanium oxide with the average major axis of 100 nm and the average minor axis of 40 nm and 0.5 g of each dispersant shown in Table 11 were added, and the dispersion was conducted with a paint shaker (zirconia beads with a diameter of 0.3 mm, filling rate: 50 vol %) for 8 hours.

The results are shown in Tables 11.

TABLE 11

| | Test example | |
|---|---|---|
| | Dispersants | Long-term stability |
| Test example 10-1: | Biterminally-Siliconized Polyglycerin (Preparation Example 1) | ◯ |
| Test example 10-2: | Biterminally-Siliconized Polyglycerin (Preparation Example 2) | ◯ |
| Test example 10-3: | Biterminally-Siliconized Polyglycerin (Preparation Example 3) | ◯ |
| Test example 10-4: | Trimethylsiloxy silicate (BY11-018 ™: Dow Corning Toray Co., Ltd) | X |
| Test example 10-5: | Amino modified silicone (KF8004 ™: Shin-Etsu Chemical Co., Ltd) | Δ |
| Test example 10-6: | Carboxyl modified silicone (X22-3701E ™: Shin-Etsu Chemical Co., Ltd) | X |
| Test example 10-7: | Polyether modified silicone (KF6017 ™: Shin-Etsu Chemical Co., Ltd) | X |

As shown in Test Examples 10-1 to 10-3, when biterminally-siliconized polyglycerins were used as a dispersant, dispersions with good long-term stability could be obtained. On the other hand, when other dispersants were used, the aggregation and precipitation of powder took place over time though the aggregates were not observed immediately after dispersion.

Thus, it was confirmed that the use of a biterminally-siliconized polyglycerin as a dispersant is desirable.

Biterminally-siliconized polyglycerins of Preparation Examples 1 to 3 were synthesized as follows.

Preparation Example 1

Synthesis of Biterminally-Siliconized Polyglycerin

Into a reaction vessel, 100 g of dimethylpolysiloxane with a hydrogen residue on one terminal (the other terminal is —Si(CH$_3$)$_2$C$_4$H$_9$, MW≈4600), 3.5 g of polyglycerin (3) diallyl ether, and 100 g of isopropyl alcohol were loaded, 0.05 g of 3% platinic chloride isopropyl alcohol solution was added, and the reaction was carried out at 80° C. for 5 hours. Subsequently, 1.5 g of 0.01 N HCl aqueous solution was added, and the hydrolysis was carried out at 60° C. for 3 hours. Then neutralization was carried out by adding 0.2 g of 1% sodium bicarbonate aqueous solution. The reaction solution was concentrated by evaporation, and the desired compound (Preparation Example 1), which was a fluid viscous liquid, was obtained.

Preparation Example 2

Synthesis of Biterminally-Siliconized Polyglycerin

Into a reaction vessel, 100 g of dimethylpolysiloxane with a hydrogen residue on one terminal (the other terminal is —Si(CH$_3$)$_2$C$_4$H$_9$, MW≈4600), 4.3 g of polyglycerin (4) diallyl ether, and 100 g of isopropyl alcohol were loaded, 0.05 g of 3% platinic chloride isopropyl alcohol solution was added, and the reaction was carried out at 80° C. for 5 hours. Subsequently, 1.5 g of 0.01 N HCl aqueous solution was added, and the hydrolysis was carried out at 60° C. for 3 hours. Then neutralization was carried out by adding 0.2 g of 1% sodium bicarbonate aqueous solution. The reaction solution was concentrated by evaporation, and the desired compound (Preparation Example 2), which was a fluid viscous liquid, was obtained.

Preparation Example 3

Synthesis of Biterminally-Siliconized Polyglycerin

Into a reaction vessel, 100 g of dimethylpolysiloxane with a hydrogen residue on one terminal (the other terminal is —Si(CH$_3$)$_2$C$_4$H$_9$, MW≈7600), 2.6 g of polyglycerin (4) diallyl ether, and 100 g of isopropyl alcohol were loaded, 0.05 g of 3% platinic chloride isopropyl alcohol solution was added, and the reaction was carried out at 80° C. for 5 hours. Subsequently, 1.5 g of 0.01 N HCl aqueous solution was added, and the hydrolysis was carried out at 60° C. for 3 hours. Then neutralization was carried out by adding 0.2 g of 1% sodium bicarbonate aqueous solution. The reaction solution was concentrated by evaporation, and the desired compound (Preparation Example 3), which was a fluid viscous liquid, was obtained.

Figure 3:
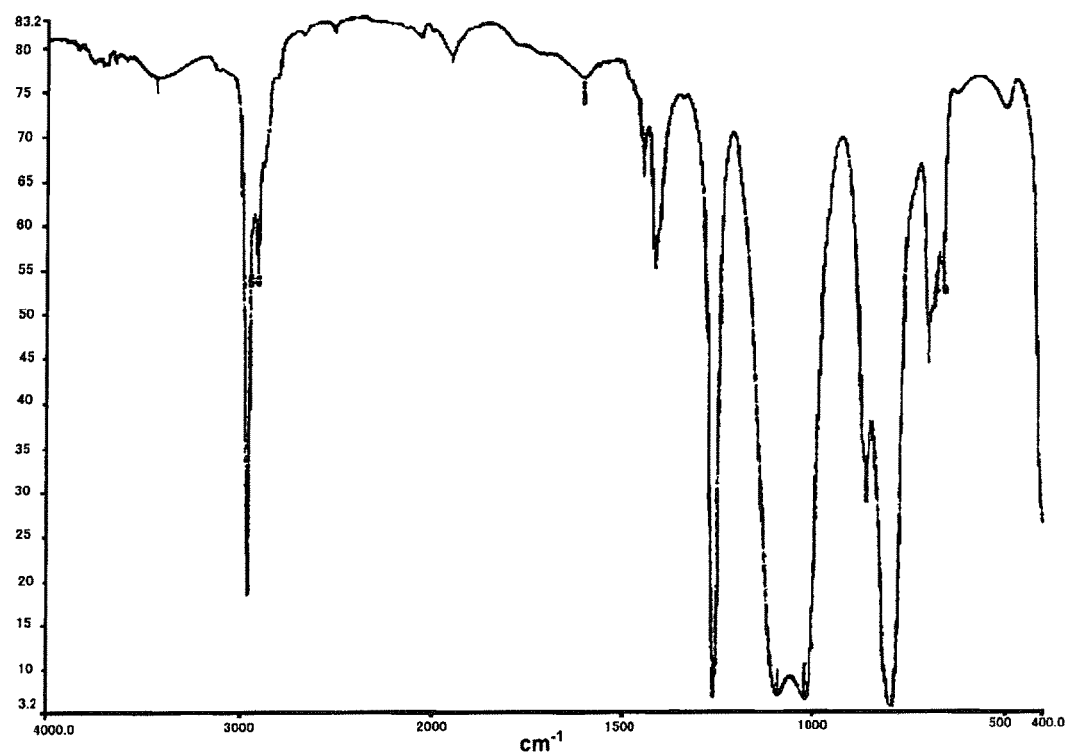
FIG. 3 shows an IR spectrum of the biterminally-siliconized polyglycerin synthesized in Preparation Example 1.

The synthesis scheme for the above-described Preparation Examples 1 to 3 is shown in FIG. 1. An IR spectrum for the product of Preparation Example 1 is shown in FIG. 3. In the spectrum, peaks due to polydimethylsiloxane were observed in the vicinities of 800, 1000, 1260, and 2960 cm$^{-1}$, respectively, and a peak due to secondary alcohols in the polyglycerin was observed in the vicinity of 1400 cm$^{-1}$. Thus, it is clear that the synthesis proceeded according to the scheme and the desired compound was obtained.

In the following, the preferable examples of cosmetics of the present invention are listed. However, the present invention is not limited by these examples. In all cosmetics, a natural finish feeling with a feeling of transparency could be achieved. In addition, an excellent UV protective effect in both UVA and UVB regions could be achieved.

| Embodiment 3 Water-in-oil type emulsified sunscreen | |
|---|---|
| | (% by weight) |
| (Oil phase components) | |
| Decamethyl cyclopentasiloxane | 20 |
| Dimethylpolysiloxane | 5 |
| Polyoxyethylene-Methylpolysiloxane copolymer | 1.5 |
| Organic modified bentonite | 0.5 |
| 2-ethylhexanoic acid cetyl | 5.0 |
| Octyl para-methoxycinnamate | 5.0 |
| Dispersion of microparticulate titanium oxide of the present invention (40%) | 25 |
| Perfume | proper quantity |
| (Water phase components) | |
| Dipropylene glycol | 5 |
| Antiseptic | proper quantity |
| Ion exchange water | remainder |

| Embodiment 4 Water-in-oil type emulsified sunscreen | |
|---|---|
| | (% by weight) |
| (Oil phase components) | |
| Dispersion of microparticulate titanium oxide of the present invention (40%) | 25 |
| Octyl para-methoxycinnamate | 5.0 |
| Methylphenylpolysiloxane | 5 |
| (Water phase components) | |
| Dipropylene glycol | 5 |
| EO-PO block copolymer | 1.5 |
| Sodium carboxymethyl cellulose | 0.15 |
| Succinoglycan | 0.35 |
| Buffer | proper quantity |
| Chelator | proper quantity |
| Antiseptic | proper quantity |
| Ion exchange water | remainder |

What is claimed is:

1. A dispersion comprising microparticulate titanium oxide dispersed in a hydrophobic dispersion medium, wherein the dispersed microparticulate titanium oxide has an average major axis of 30 to 100 nm, an average minor axis of 8 to 50 nm, and an average particle size of 80 to 110 nm, and wherein the dispersion further comprises biterminally-siliconized polyglycerin as a dispersant.

2. The dispersion according to claim 1, wherein the hydrophobic dispersion medium comprises silicone oil, and wherein the silicone oil content of the hydrophobic dispersion medium is 10 to 100 percent by weight.

3. A cosmetic comprising the dispersion according to claim 1.

4. A cosmetic comprising the dispersion according to claim 2.

* * * * *